US008828019B1

(12) United States Patent
Raymond et al.

(10) Patent No.: US 8,828,019 B1
(45) Date of Patent: Sep. 9, 2014

(54) INSERTER FOR EXPANDING AN EXPANDABLE INTERBODY FUSION DEVICE

(71) Applicant: Spine Wave, Inc., Shelton, CT (US)

(72) Inventors: Spanky Allen Raymond, Uniontown, OH (US); Scott McLean, Waterbury, CT (US); Nicola Cullinan, Bethel, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 13/799,792

(22) Filed: Mar. 13, 2013

(51) Int. Cl.
A61B 17/58 (2006.01)
A61B 17/60 (2006.01)
A61F 2/00 (2006.01)
A61F 2/46 (2006.01)

(52) U.S. Cl.
CPC .................................. *A61F 2/4611* (2013.01)
USPC ........................... 606/99; 606/105; 623/17.15

(58) Field of Classification Search
USPC ............................................ 606/99, 105, 914
See application file for complete search history.

(56) References Cited

U.S. PATENT DOCUMENTS

| 3,486,505 | A | 12/1969 | Morrison |
| 4,524,766 | A | 6/1985 | Petersen |
| 4,683,476 | A | 7/1987 | Ferrari et al. |
| 4,736,738 | A | 4/1988 | Lipovsek et al. |
| 4,743,493 | A | 5/1988 | Sioshansi et al. |
| 4,755,797 | A | 7/1988 | Kanaya |
| 4,863,476 | A | 9/1989 | Shepperd |
| 4,888,024 | A | 12/1989 | Powlan |
| 5,059,193 | A | 10/1991 | Kuslich |
| 5,192,326 | A | 3/1993 | Bao et al. |
| 5,192,327 | A | 3/1993 | Brantigan |
| 5,197,971 | A | 3/1993 | Bonutti |
| 5,298,254 | A | 3/1994 | Prewett et al. |
| 5,431,658 | A | 7/1995 | Moskovich |
| 5,439,684 | A | 8/1995 | Prewett et al. |
| 5,505,732 | A | 4/1996 | Michelson |
| 5,514,180 | A | 5/1996 | Heggeness et al. |
| 5,522,899 | A | 6/1996 | Michelson |

(Continued)

FOREIGN PATENT DOCUMENTS

| EP | 0621020 A1 | 10/1994 |
| FR | 2639823 A1 | 6/1990 |
| FR | 2719763 A1 | 11/1995 |
| WO | 9902214 A1 | 1/1999 |

OTHER PUBLICATIONS

PCT Search Report for corresponding PCT Application No. PCT/US2008/064534.

(Continued)

*Primary Examiner* — Andrew Yang
(74) *Attorney, Agent, or Firm* — Hoffmann & Baron, LLP

(57) ABSTRACT

An elongate inserter has a distal end releasably connected to an expandable interbody fusion device and a proximal end including a trigger actuator. The interbody fusion device comprises a superior endplate and an inferior endplate that are movable in an expansion direction relative to each other in the intradiscal space. The inserter includes a lifting platform and an elevator that define cooperatively engaging ramps and ramps surfaces that upon operation of the trigger actuator cause the superior and inferior endplates to move relatively away from each other. A driver is supported by the inserter for pushing an insert into the expanded device between the superior and inferior endplates.

30 Claims, 10 Drawing Sheets

(56) References Cited

U.S. PATENT DOCUMENTS

| | | |
|---|---|---|
| 5,571,109 A | 11/1996 | Bertagnoli |
| 5,591,235 A | 1/1997 | Kuslich |
| 5,645,599 A | 7/1997 | Samani |
| 5,702,454 A | 12/1997 | Baumgartner |
| 5,755,797 A | 5/1998 | Baumgartner |
| 5,756,127 A | 5/1998 | Grisoni et al. |
| 5,766,252 A | 6/1998 | Henry et al. |
| 5,836,948 A | 11/1998 | Zucherman et al. |
| 5,860,977 A | 1/1999 | Zucherman et al. |
| 5,891,147 A | 4/1999 | Moskovitz et al. |
| 5,951,553 A | 9/1999 | Betz et al. |
| 5,980,522 A | 11/1999 | Koros et al. |
| 6,033,411 A | 3/2000 | Preissman |
| 6,045,579 A | 4/2000 | Hochshuler et al. |
| 6,066,154 A | 5/2000 | Reiley et al. |
| 6,074,390 A | 6/2000 | Zucherman et al. |
| 6,110,179 A | 8/2000 | Flivik et al. |
| 6,110,210 A | 8/2000 | Norton et al. |
| 6,159,211 A | 12/2000 | Boriani et al. |
| 6,159,244 A | 12/2000 | Suddaby |
| 6,183,517 B1 | 2/2001 | Suddaby |
| 6,190,414 B1 | 2/2001 | Young et al. |
| 6,200,347 B1 | 3/2001 | Anderson et al. |
| 6,241,771 B1 | 6/2001 | Gresser et al. |
| 6,273,916 B1 | 8/2001 | Murphy |
| 6,279,916 B1 | 8/2001 | Stecher |
| 6,287,308 B1 | 9/2001 | Betz et al. |
| 6,287,309 B1 | 9/2001 | Baccelli et al. |
| 6,290,724 B1 | 9/2001 | Marino |
| 6,387,130 B1 | 5/2002 | Stone et al. |
| 6,395,034 B1 | 5/2002 | Suddaby |
| 6,402,750 B1 | 6/2002 | Atkinson et al. |
| 6,419,705 B1 | 7/2002 | Erickson |
| 6,432,107 B1 | 8/2002 | Ferree |
| 6,436,142 B1 | 8/2002 | Paes et al. |
| 6,478,800 B1 | 11/2002 | Fraser et al. |
| 6,488,710 B2 | 12/2002 | Besselink |
| 6,500,205 B1 | 12/2002 | Michelson |
| 6,520,993 B2 | 2/2003 | James et al. |
| 6,562,074 B2 | 5/2003 | Gerbec et al. |
| 6,595,998 B2 | 7/2003 | Johnson et al. |
| 6,620,196 B1 | 9/2003 | Trieu |
| 6,648,917 B2 | 11/2003 | Gerbec et al. |
| 6,656,178 B1 | 12/2003 | Veldhuizen et al. |
| 6,726,691 B2 | 4/2004 | Osorio et al. |
| 6,740,093 B2 | 5/2004 | Hochschuler et al. |
| 6,837,904 B2 | 1/2005 | Ralph et al. |
| 6,852,095 B1 | 2/2005 | Ray |
| 6,852,126 B2 | 2/2005 | Ahlgren |
| 6,852,129 B2 | 2/2005 | Gerbec et al. |
| 6,863,673 B2 | 3/2005 | Gerbec et al. |
| 6,997,929 B2 | 2/2006 | Manzi et al. |
| 7,118,580 B1 | 10/2006 | Beyersdorff et al. |
| 7,591,852 B2 | 9/2009 | Prosser |
| 7,722,625 B2 * | 5/2010 | Sanders et al. ............... 606/105 |
| 7,931,688 B2 | 4/2011 | Landry et al. |
| 7,967,867 B2 | 6/2011 | Barreiro et al. |
| 8,062,375 B2 | 11/2011 | Glerum et al. |
| 8,308,805 B2 | 11/2012 | Lynn et al. |
| 8,382,842 B2 | 2/2013 | Greenhalgh et al. |
| 8,628,578 B2 | 1/2014 | Miller et al. |
| 2002/0026195 A1 | 2/2002 | Layne et al. |
| 2002/0147497 A1 | 10/2002 | Belef et al. |
| 2002/0177897 A1 | 11/2002 | Michelson |
| 2003/0171812 A1 | 9/2003 | Grunberg et al. |
| 2004/0019354 A1 | 1/2004 | Johnson et al. |
| 2004/0030387 A1 | 2/2004 | Landry et al. |
| 2004/0064144 A1 | 4/2004 | Johnson et al. |
| 2004/0220580 A1 | 11/2004 | Johnson et al. |
| 2005/0027364 A1 | 2/2005 | Kim et al. |
| 2005/0149194 A1 | 7/2005 | Ahlgren |
| 2006/0058807 A1 | 3/2006 | Landry et al. |
| 2006/0058880 A1 | 3/2006 | Wysocki et al. |
| 2006/0129244 A1 | 6/2006 | Ensign |
| 2008/0154377 A1 | 6/2008 | Voellmicke |
| 2008/0172127 A1 | 7/2008 | Perez-Cruet et al. |
| 2009/0198339 A1 | 8/2009 | Kleiner et al. |
| 2011/0184522 A1 | 7/2011 | Melkent et al. |
| 2012/0158144 A1 | 6/2012 | Ullrich, Jr. et al. |
| 2013/0090735 A1 | 4/2013 | Mermuys et al. |

OTHER PUBLICATIONS

Baddeley, S. and Cullen, J.C., "The Use of Methylmethacrylate in the Treatment of Giant Cell Tumours of the Proximal Tibia", Aust. N.Z. J. Surg. vol. 49—No. 1, Feb. 1979, 3 pp.

Campanacci, M., Gui, L., Ranieri, L., Savini, R., "Treatment of Tibial Plateau Fractures", Chi. Org. Mov. 72(3), Dec. 1975 (Italian text), pp. 234-256, English Translation, 15 pp.

Kyphon Inc., Surgical Technique Manual Nov. 16, 1999, pp. 5, 6, 9, 16-19.

Kyphon Vertebral Treatment Notebook, date unknown, 9 pp.

Kyphon web page, www.kyphon.com, Mar. 13, 2001, 1 p.

AOM Technique Manual, "Controlled Delivery for Osteoplasty, A Vertebroplasty Application", Cat #900.001—Rev B—date unknown.

Medtronic Sofamor Danek, "Verte-Stack™, Peek Stackable Corpectomy Device, Surgical Technique", date unknown, 8 pp.

Signus Medical, Tetris, Sep. 2003, 1 p.

Blackstone Medical Inc., Construx™ Peek VBR System, 2005, www.blackstonemedical.com, 1 p.

Globus Medical, Sustain™ R Small, date unknown, 6 pp.

U.S. Appl. No. 13/795,054, entitled "Expandable Interbody Fusion Device with Graft Chambers", filed Mar. 12, 2013.

* cited by examiner

INSERTER FOR EXPANDING AN EXPANDABLE INTERBODY FUSION DEVICE

FIELD OF THE INVENTION

The subject invention relates generally to the field of spinal implants and more particularly to an inserter for expanding an expandable interbody fusion device and inserting an insert therewithin.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

Certain spinal devices for achieving fusion are also expandable so as to correct disc height between the adjacent vertebrae. Examples of expandable interbody fusion devices are described in U.S. Pat. No. 6,595,998 entitled "Tissue Distraction Device", which issued on Jul. 22, 2003 (the '998 patent), U.S. Pat. No. 7,931,688 entitled "Expandable Interbody Fusion Device", which issued on Apr. 26, 2011 (the '688 patent), and U.S. Pat. No. 7,967,867 entitled "Expandable Interbody Fusion Device", which issued on Jun. 28, 2011 (the '867 patent). The '998 patent, the '688 patent and the '867 patent each discloses sequentially introducing in situ a series of elongate inserts referred to as wafers in a percutaneous approach to incrementally distract opposing vertebral bodies to stabilize the spine and correct spinal height, the wafers including features that allow adjacent wafers to interlock in multiple degrees of freedom. The '998 patent, the '688 patent and the '867 patent are assigned to the same assignee as the present invention, the disclosures of these patents being incorporated herein by reference in their entirety.

One issue that has arisen regarding such interbody fusion devices that use inserts or wafers to incrementally expand such devices is the determination of when full expansion has been achieved as a result of ligamentotaxis and no further inserts may be inserted. It is therefore desirable for a surgeon to know when a sufficient number of inserts has been introduced to stabilize the spine and correct spinal height and whether any additional inserts may be introduced.

Accordingly, there is a need for a method and instrument to expand an expandable interbody fusion device and introduce inserts therein and to determine when proper expansion of the device has been achieved and no further inserts may be introduced.

SUMMARY OF THE INVENTION

It is an object of the invention to provide an inserter for expanding an expandable spinal implant, such as an interbody fusion device and to introduce inserts therein after the implant has been expanded. It is a further object of the invention to also provide a method whereby full expansion of the expandable device may be determined in a manner such that a user may ascertain that no additional inserts may be inserted.

DESCRIPTION OF THE EMBODIMENTS

Figure 1:
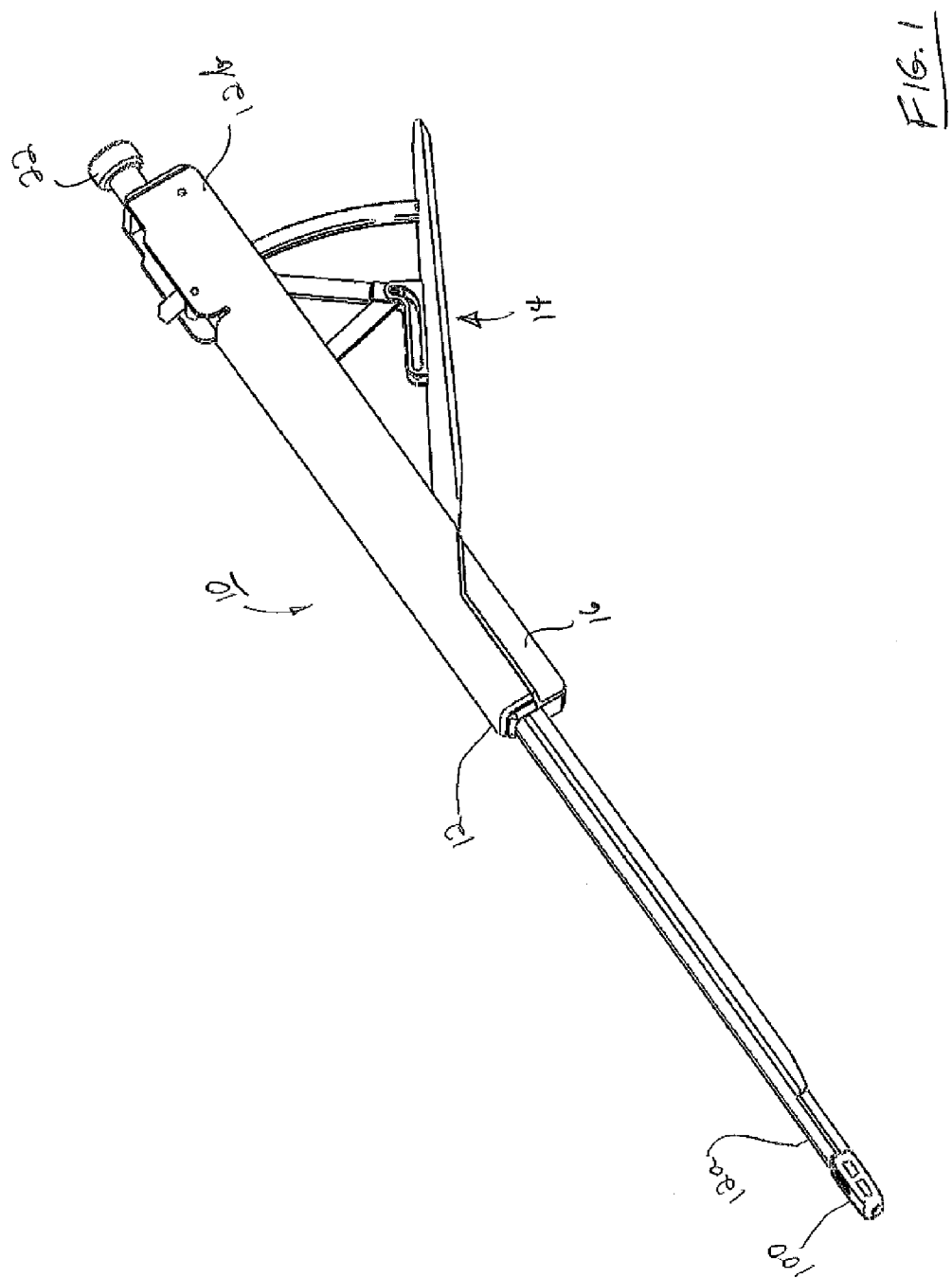
FIG. 1 is a top perspective of an inserter in accordance with one embodiment of the present invention releasably attached to and expandable interbody fusion device, shown unexpanded.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
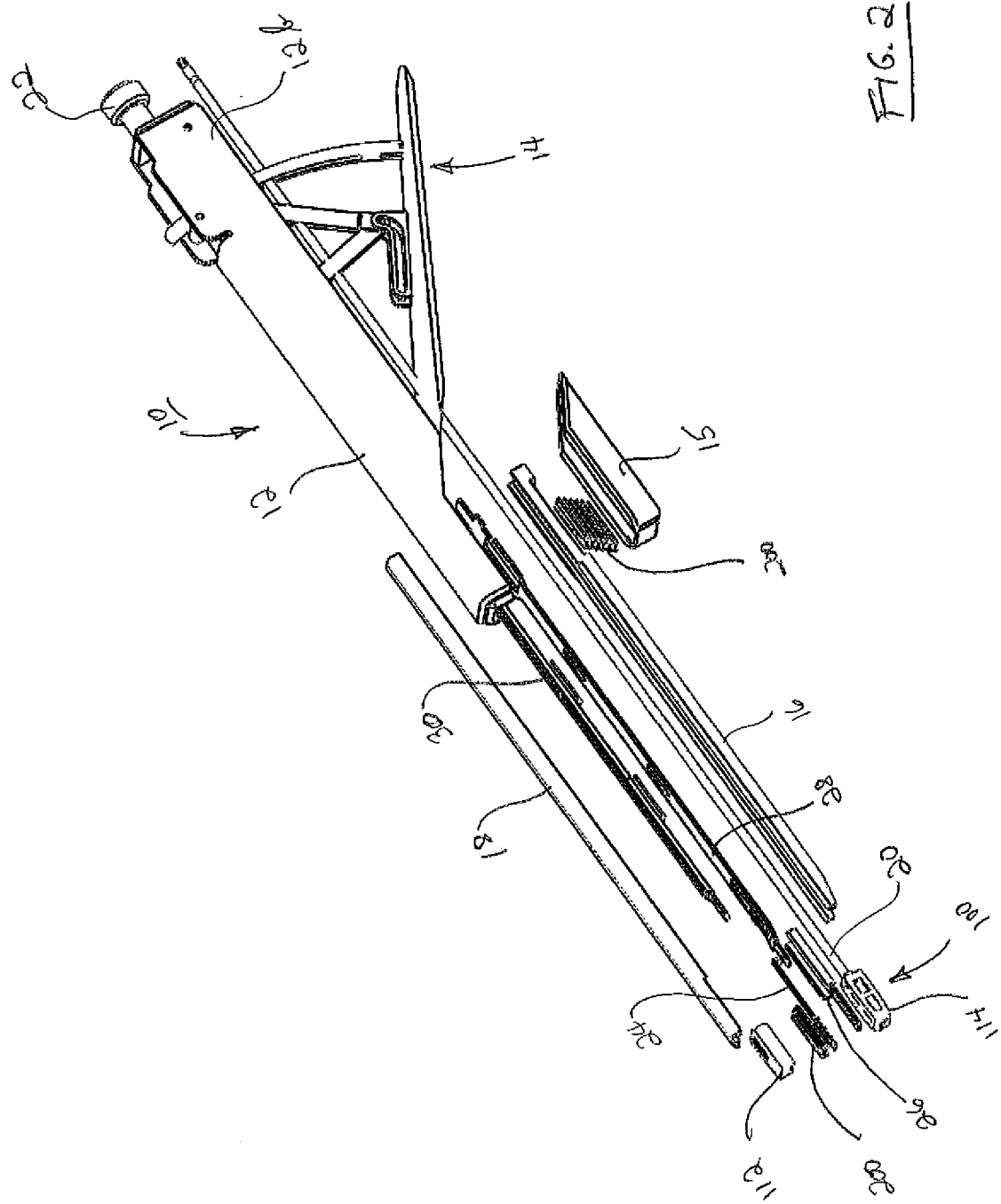
FIG. 2 is an exploded perspective view of the distal end of the inserter of FIG. 1.
Figure 3:
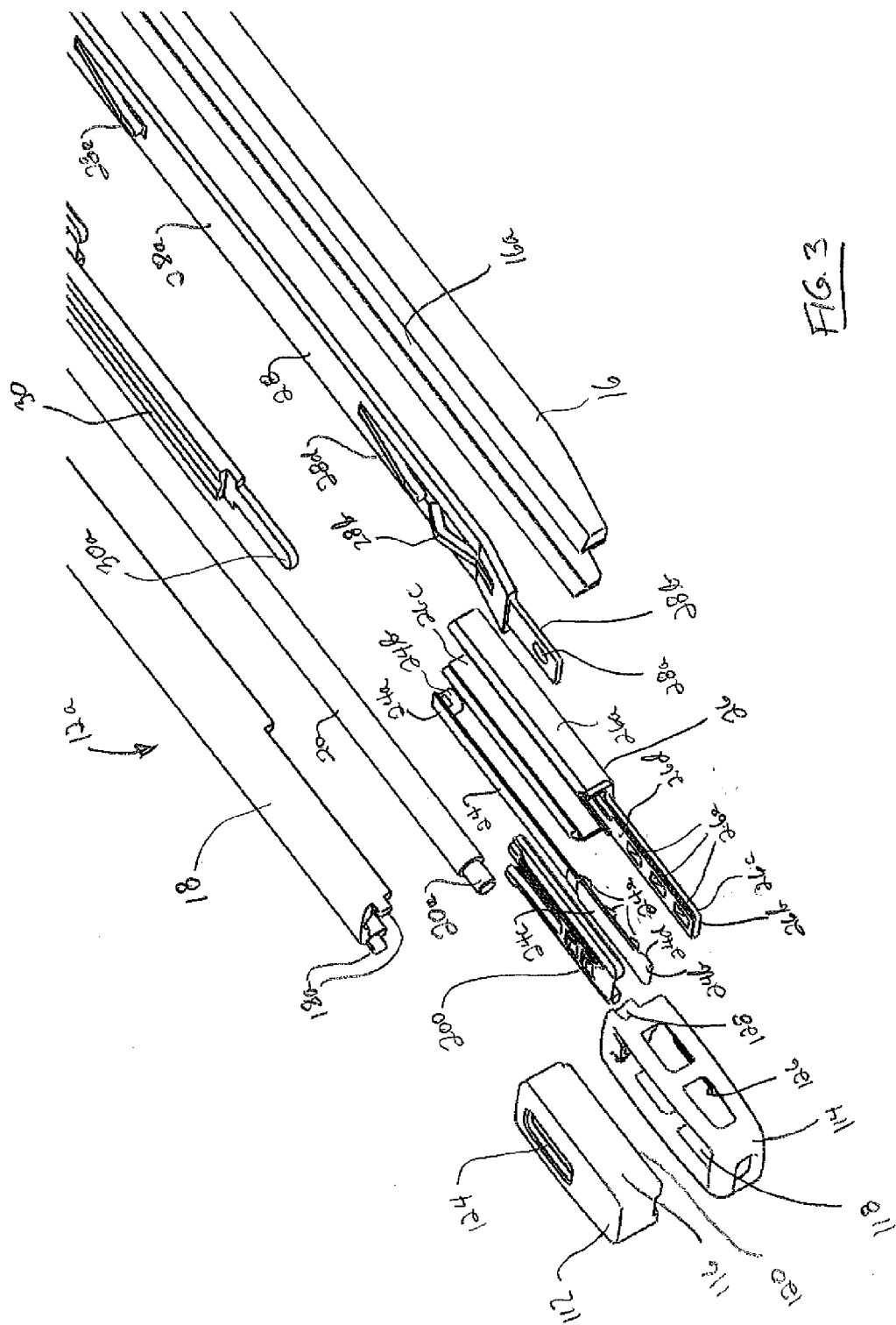
FIG. 3 is an enlarged view of the exploded portion of FIG. 2.

Turning now to FIGS. 1-3, inserter 10 is shown for use in expanding in situ a spinal implant, such as an interbody fusion device 100, and for inserting inserts into the expanded device 100. The expandable interbody fusion device 100 includes a first element, such as superior endplate 112 and a second element, such as inferior endplate 114, as shown in FIGS. 2-3. The height across the superior and inferior endplates 112, 114 in the unexpanded condition as illustrated in FIG. 1 is less than the normal anatomic height of a typical intradiscal space. The invention contemplates expanding the interbody fusion device 100 by the inserter 10 to ultimately restore the normal anatomic height of the disc space and thereafter inserting a series of inserts, such as interlocking inserts 200, as will be described, to form a stack of inserts 200 between the expanded superior and inferior endplates.

The superior endplate 112 is elongate and comprises a hub 116 that is sized and configured to fit within a cavity 118 of the inferior endplate 114 for telescoping movement therewithin upon expansion. The lower surface 120 of the hub 116 includes a shaped configuration defined by insert mating features 122 (see FIG. 7) that are substantially identical to the mating features on the lower surface of each insert 200, as will be described. The superior endplate 112 includes a graft chamber defined by an opening 124 extending therethrough and inferior endplate 114 includes a graft chamber defined by an opening 126 extending therethrough for receipt of a suitable bone filler or bone graft to promote fusion between opposing vertebral bodies of a spine. Further details of interbody fusion device 100 are described in commonly assigned U.S. patent application Ser. No. 13/795,054 entitled "Expandable Interbody Fusion Device with Graft Chambers", filed on Mar. 12, 2013 ("the '054 Application") and incorporated herein by reference.

Figure 5:
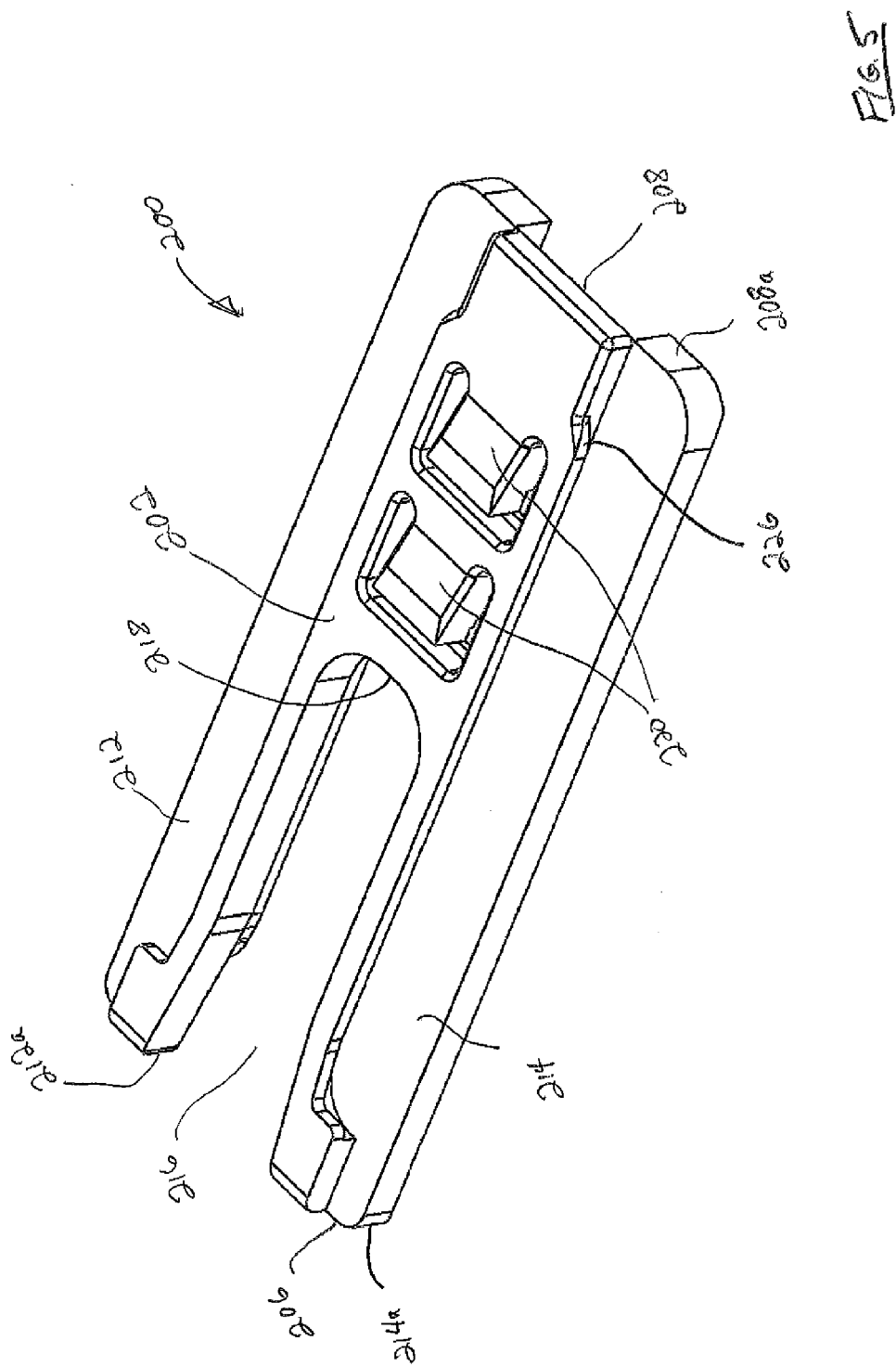
FIG. 5 is a top perspective view of an insert used in an expandable spinal interbody fusion device of the subject invention.
Figure 6:
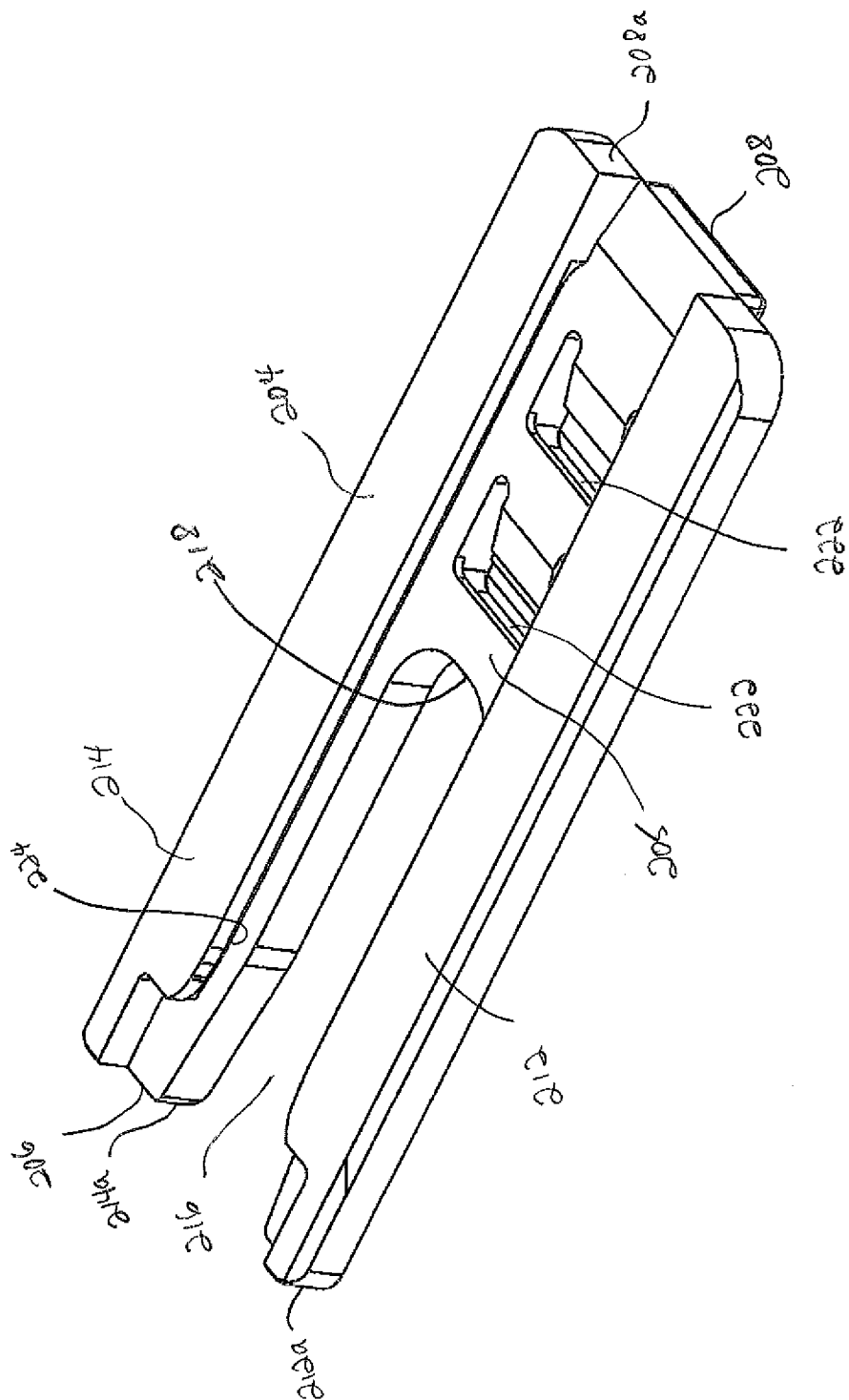
FIG. 6 is a bottom perspective view of the insert of FIG. 5.

Details of the interlocking insert 200 are shown in FIGS. 5-6. The insert 100 is elongate and has an upper surface 202 and a lower surface 204, both of which are generally planar so that the inserts can form a stable stack within the interbody fusion device 10 upon expansion. Insert 200 includes a trailing rear end 206 and a leading front end 208. The rear end 206 is formed substantially in the form of a horseshoe, with a pair of spaced opposing arms 212 and 214 defining an open rearward facing generally U-shaped opening 216. The surface 218 between the upper surface 202 and the lower surface 204 at the base of opening 216 defines a pushing surface 218 for receipt of a driver of inserter 10, as will be described. The opening 216 at the rear end of each insert 200 is provided to allow bone graft material to flow into the device 100 through the insert openings 216 and into the openings 124 and 126 extending through the superior endplate 112 and the inferior endplate 114, respectively. The rear end 206 includes a flat surface 212a and 214a, respectively at the free end of each arm 212 and 214 and a flat surface 208a on the leading front end 208 of the insert 200.

The insert 200 includes several features for interlocking engagement to the hub 116 and to adjacent inserts 100 in a complementary interlocking mating interface. One particular feature includes a series of locking elements defined by resiliently deflectable prongs 220 that project outwardly above the upper surface 202 of the insert 200 in the direction of expansion of device 100. A complementary series of locking surfaces 222 are defined in the lower surface 204 of the insert 200 for resilient engagement with the prongs 220 as inserts are inserted into device 100 to form a stack. The lower surface 204 of each insert 200 as shown in FIGS. 5 and 6 also defines a T-slot configuration 224 for mating with a T-bar configuration 226 on the upper surface 202 of a successive insert 100. In the illustrated arrangement, there are two prongs 220 extending generally linearly and substantially centrally along the elongate longitudinal direction adjacent the front end 208 of insert 200. The structure and function of insert 200 and the prongs 220 and locking surfaces 222 are more fully described in the '054 Application. However, unlike wafers 100 described in the '054 Application, the inserts 200 described herein do not function to assist in the separation of superior endplate 112 and inferior endplate 114 or any subsequent inserts 200 inserted into interbody fusion device 100 as that lifting and function is provided by inserter 10.

Turning again now to FIGS. 1-3, details of the inserter 10 are described. Inserter 10 comprises an elongate barrel 12 having a distal end 12a and a proximal end 12b. A trigger actuator 14 to effect expansion of device 100 and insertion of inserts 200 into device 100 after expansion is provided at the proximal end 12b of barrel 12. A cartridge 15 supported by barrel 12 on the underside thereof contains a plurality of inserts 200 to provide a supply of inserts 204 inserting into device 100 by inserter 10.

The distal end 12a is shown in exploded detail in FIGS. 2-3. The barrel 12 includes a lower track 16 and an upper track cover 18. An elongate guide pin 20 is supported by barrel 12, the distal end 20a of the guide pin 20 being threaded for releasable threaded engagement into a suitable threaded opening in the proximal end of the inferior endplate 114. The proximal end 20b of guide pin 20 is provided with a threaded knob 22 for compressing the barrel 12 and thereby the inserter to the device 100. The track cover 18, in one arrangement, includes a pair of opposing tabs 18a that engage corresponding notches 128 at the proximal end of the inferior endplate 114 to assist in rigidly securing the barrel 12 to the device 100. It should be appreciated that other securement structure may be used to releasably attach the barrel 12 and thereby inserter 10 to the device 100.

The distal end 12a of barrel 12 supports a lifting platform 24 and an elevator 26. The lifting platform 24 is coupled at its proximal end 24a by a boss 24b or other suitable projection to a lifting platform link 28. The boss 24b is suitably received and retained in opening 28a at the distal end of link 28. The lifting platform 24 is axially translatable relative to elevator 26 upon axial translational movement of link 28 which is coupled to an actuator, such as trigger actuator 14 at its proximal end, as will be described. Link 28 is supported by track 16 for translational movement within a track channel 16a extending axially along track 16. Inserts 200 are movably supported in a linear array on link 28 within the channel 16a. It should be appreciated that actuators other than trigger actuators may be used with the inserter 10 described herein.

Elevator 26 comprises a proximal end 26a and a distal projecting end 26b. The proximal end 26a is suitably affixed to the track 16 and, in the particular arrangement being described, remains in a fixed position relative to lifting platform 24 and inferior endplate 114 as lifting platform is translationally moved. The proximal end 26a defines a channel 26c for receipt of the proximal end 24a of lifting platform 24. The lifting platform 24 and elevator 26 may in one arrangement be a disposable component and replaced by a new unused lifting platform 24 and elevator 26 for subsequent procedures.

The distal projecting end 26b of elevator 26 includes a lower substantially flat surface 26c and an upper surface 26d, generally parallel to lower surface 26c. Projecting end 26b is configured to extend within inferior endplate 114 with lower surface 26c supported by an interior surface 114a (see FIG. 7). Upper surface 26d is formed to have a series of axially extending ramp surfaces 26e extending therewithin, three such ramp surfaces 26e being illustrated. Lifting platform 24 includes at its distal end 24b an upper substantially flat surface 24c and a lower surface 24d, generally parallel to upper surface 24c. Upper surface 24c is configured to engage and support surface 205 at the underside of insert 200 (see FIG. 6) as well as the lower surface 120 of superior endplate 112 which has mating features 122 that are substantially identical to the mating features on the lower surface of each insert 200. Lower surface 24d is formed to have a series of axially extending ramps 24e, three of which are shown. Ramps 24e projecting downwardly from lifting platform 24 and ramp surfaces 26e extending within elevator 26 are configured to have suitably inclined surfaces such that upon axial translational movement of lifting platform 24 relative to elevator 26 ramps 24e engage ramp surfaces 26e to cause lifting platform 24 to move upwardly and separate from elevator 26.

Lifting platform link 28 includes thereon an upper surface 28a on which the inserts 200 are movably supported in a linear array. Link 28 includes a spring element 28b having an inclined surface for engaging an insert 200 and moving such insert upwardly into an insertion position from track 16 during axial transit along link 28. A pair of cantilevered spring projections 28d and 28e may be spaced axially along link 20 in a manner to substantially prevent retrograde movement of inserts 200 along link 28.

Barrel 12 further supports a driver 30 for axial translational movement within the barrel 12. The proximal end of driver 30 is coupled to trigger actuator 14 to effect translational movement of the driver, as will be described. The distal end of driver 30 comprises a pushing surface 30a sized and configured to enter into the opening 216 of an insert 200 to engage pushing surface 218 and push the insert 200 into the device 100 upon axial distal movement of driver 30.

Figure 4:
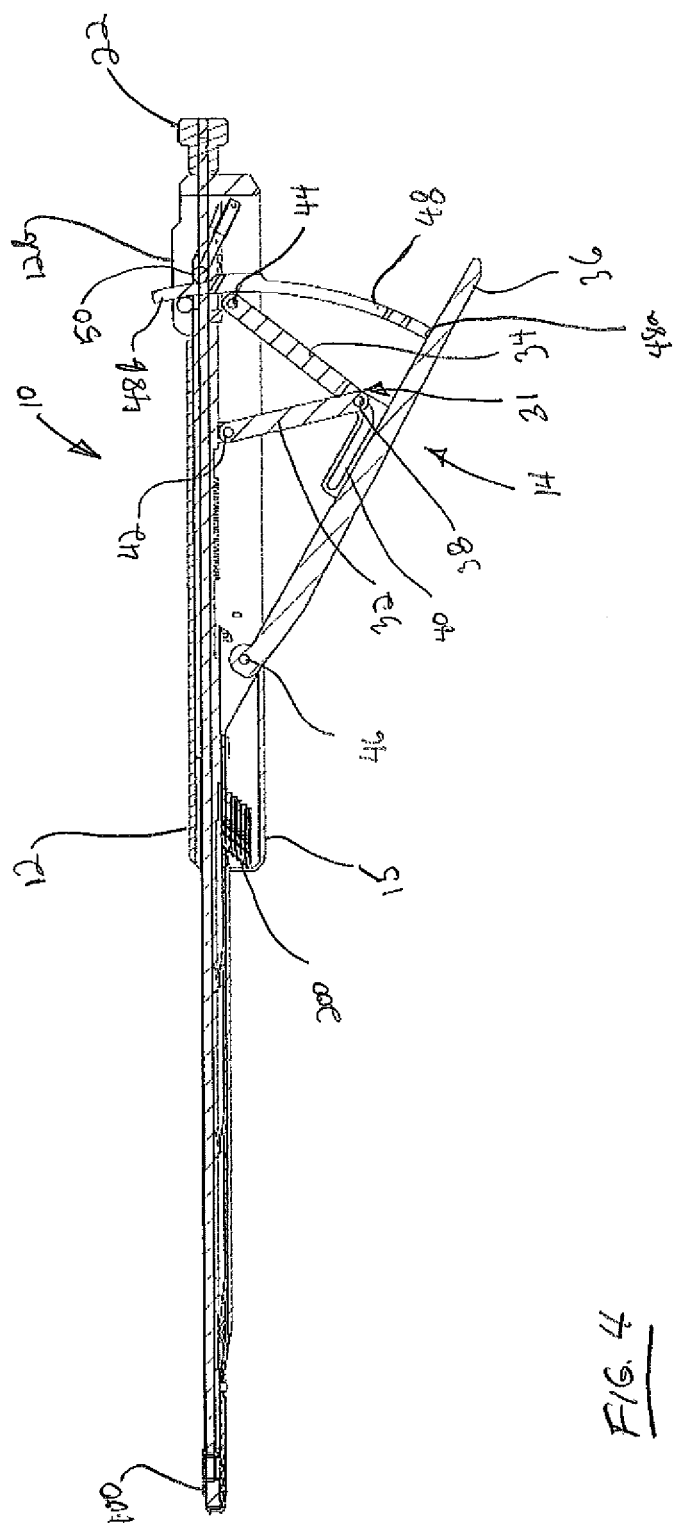
FIG. 4 is a longitudinal cross-sectional view of the inserter of FIG. 1.

Turning now to FIG. 4, the details of the trigger actuator 14 of the inserter 10 and its function are described. Trigger actuator 14 comprises a bar linkage mechanism 31 comprising a first bar 32 and a second bar 34. The lower end of each bar 32 and 34 is pivotally connected to a handle 36 by a pivot pin 38. Pin 38 slides within a cam track 40 supported on handle 36. The upper end of bar 32 is pivotally connected to the proximal end of driver 38 pivot pin 42. The upper end of bar 34 is pivotally connected to the proximal end 12b of barrel 12 by a pivot pin 44. Handle 36 is pivotally connected to barrel 12 by a pivot pin 46. A curved cam member 48 is attached at its lower end 48a to handle 36 with upper end 48b extending though barrel 12. Cam member 48 upon squeezing movement of the handle 36 toward barrel 12 engages a cam following surface 50 on barrel 12 to initially pull lifting platform link proximally. The bar linkage mechanism 31 of the trigger actuator 14 is structured to move lifting platform link 28 and driver 30 independently of each other and with suitable time delays between such movements based on the configuration of the cam track 40. The driver 30 is returned to its original starting position when the handle 36 is released. Thus, during a single stroke operation of trigger actuator 14 the lifting platform 24 is lifted relative to elevator 26, driver 30 pushes an insert 200 into the device 100, lifting platform 24 is retracted relatively toward elevator 26 and finally driver 30 is retracted from device 100. Such single stroke of operation is initiated when handle 36 is in the starting position of FIG. 4 and is completed when handled 36 is released and returns to its starting position.

Figure 7:
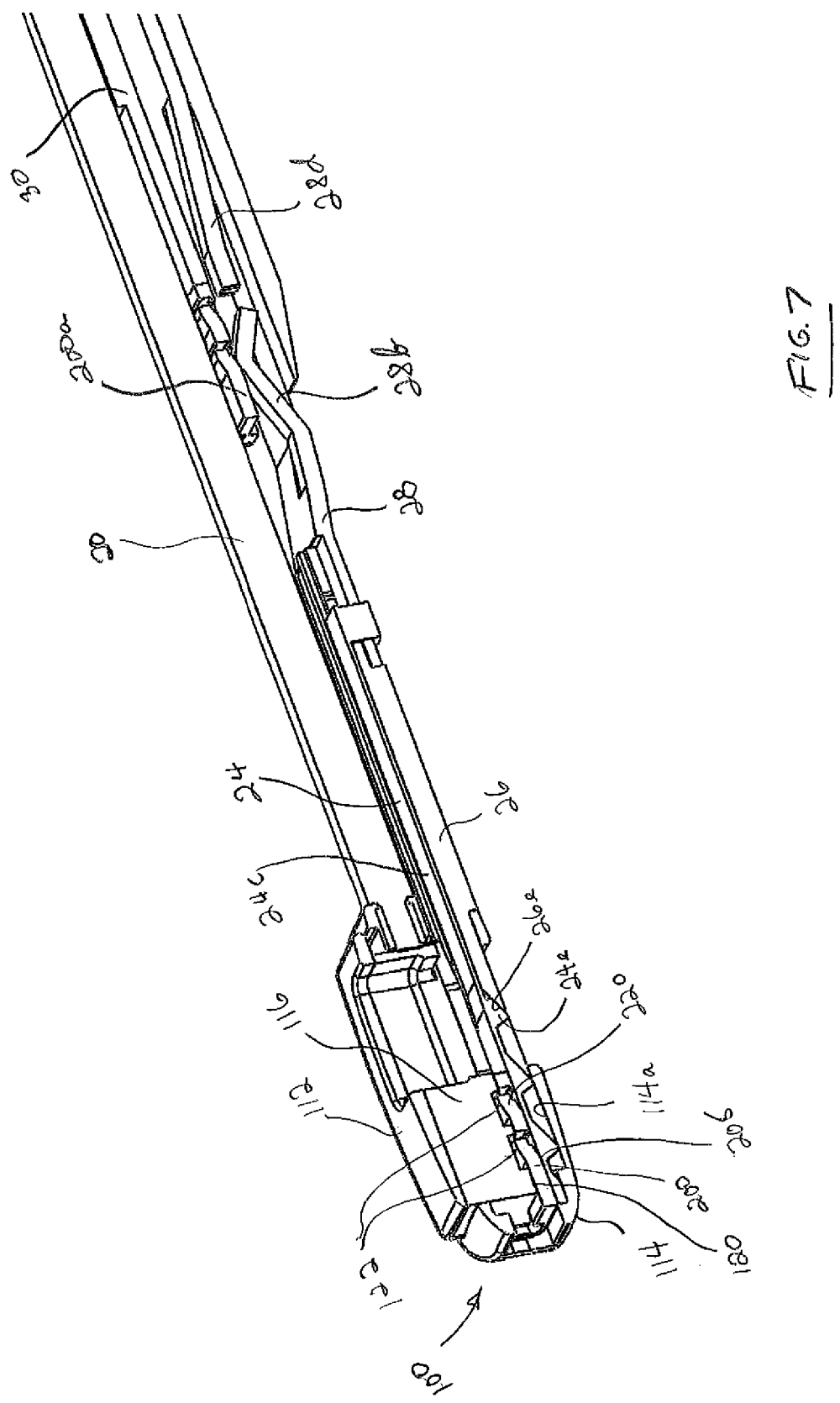
FIG. 7 is a partial perspective cross sectional view of the inserter of FIG. 1 releasably attached to an expandable interbody fusion device with a first insert of FIG. 5 having been inserted therein.
Figure 8:
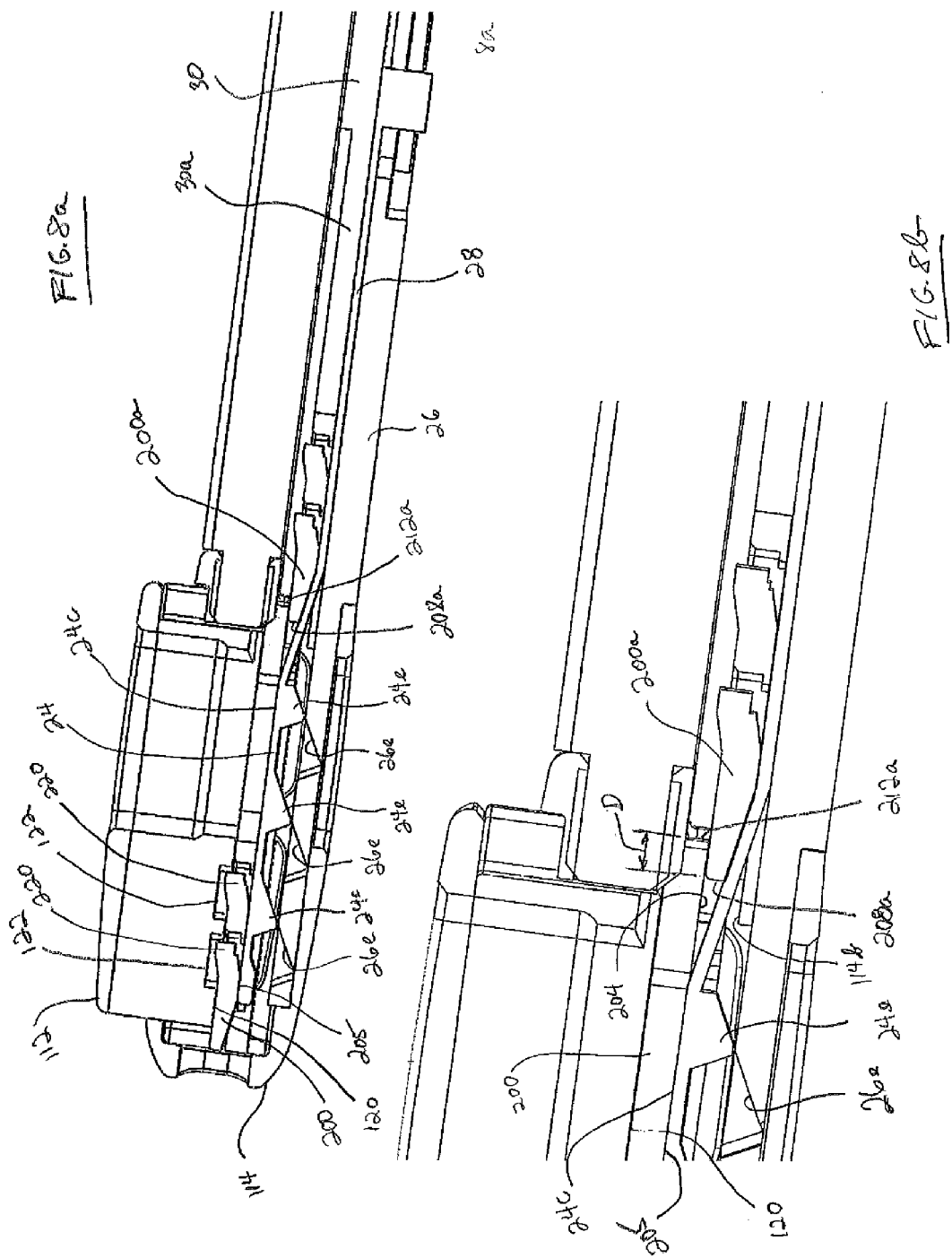
FIG. 8a is a partial side perspective view of the inserter and expandable interbody fusion device bottom of FIG. 7 showing a second insert entering the interbody fusion device at the proximal end and below the first insert.
FIG. 8b is an enlarged view of a portion of FIG. 8a showing the relative positions of the first and second inserts.
Figure 9:
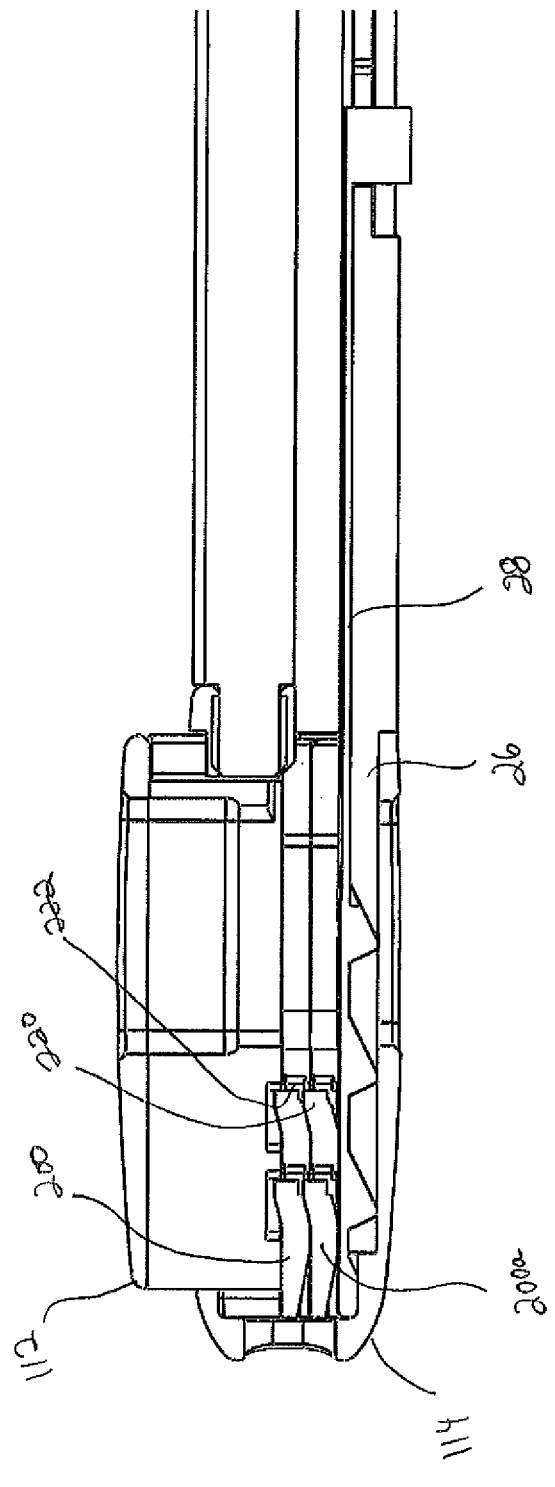
FIG. 9 is a partial side perspective view of the inserter and expandable interbody fusion device of FIG. 8a showing the second insert fully inserted into the interbody fusion device.

Turning now to FIGS. 7-9 the use of inserter 10 to expand the device 100 and insert one or more inserts 200 to form an interlock stack is further described. FIG. 7 illustrates a condition of the expansion of device 100 wherein a first insert 200 has been positioned between superior endplate 112 and inferior endplate 114 with prongs 220 suitably interlockingly engaging the mating features 122 at the lower surface of hub 116. It should be understood that to insert the first insert 200 the inserter 10 and the method described herein were similarly employed. A subsequent insert 200a is shown on spring element 28b with the insert 200a having been lifted by spring element 28b into an insertion position from channel 16a of track 16 during axial advancement distally by driver 30. In this condition the ramps 24e of lifting platform 24 are not deployed relative to ramp surfaces 26e of elevator 26. Upper surface 24c of lifting platform 24 is in contact with and supports the underside surface 205 of insert 200.

Upon operation of trigger actuator 14, lifting platform link 28 is translated proximally causing ramps 24e to engage and ride upwardly along ramp surfaces 26e of elevator 26 thereby causing during such translational movement the lifting platform 24 to move upwardly and away from elevator 26. Such movement lifts insert 200 together with interlocked superior endplate 112 in the direction of expansion an incremental distance slightly greater than the thickness of insert 200a. With the bar linkage mechanism 31 of trigger actuator 14 configured to temporarily hold this position for a certain period of time, continued operation of trigger actuator 14 moves driver 30 distally until the pushing surface 30a of driver 30 causes the front end 208a of subsequent insert 200a to enter device 100 between lower surface 204 of a previously inserted insert 200 and inferior ledge 114b of the inferior endplate 114, as shown in FIGS. 8a and 8b. At a point when front end 208a has entered a certain distance, D, continued operation of trigger actuator 14 causes lifting platform link 28 to translate distally causing ramps 24e to slide downwardly along ramp surfaces 26e thereby retracting lifting platform 24 toward elevator 26. Further operation of trigger actuator 14 causes driver 30 to move axially distally pushing insert 200a fully into device 100 with little further resistance until the prongs 220 engage locking surfaces 222. As illustrated in FIG. 9, once insert 200a is completely inserted prongs 220 suitably interlock with locking surfaces 222 of previously inserted insert 200. When handle 36 is released the driver 30 is drawn proximally a sufficient distance within barrel 12 to be positioned to receive another insert 200b supported within track channel 16a, if necessary. For illustrative purposes, wherein inserts 200 and 200a each have a length of approximately 25 mm in the thickness of approximately 1 mm, distance D may be a minimum of approximately 2-3 mm.

Figure 10:
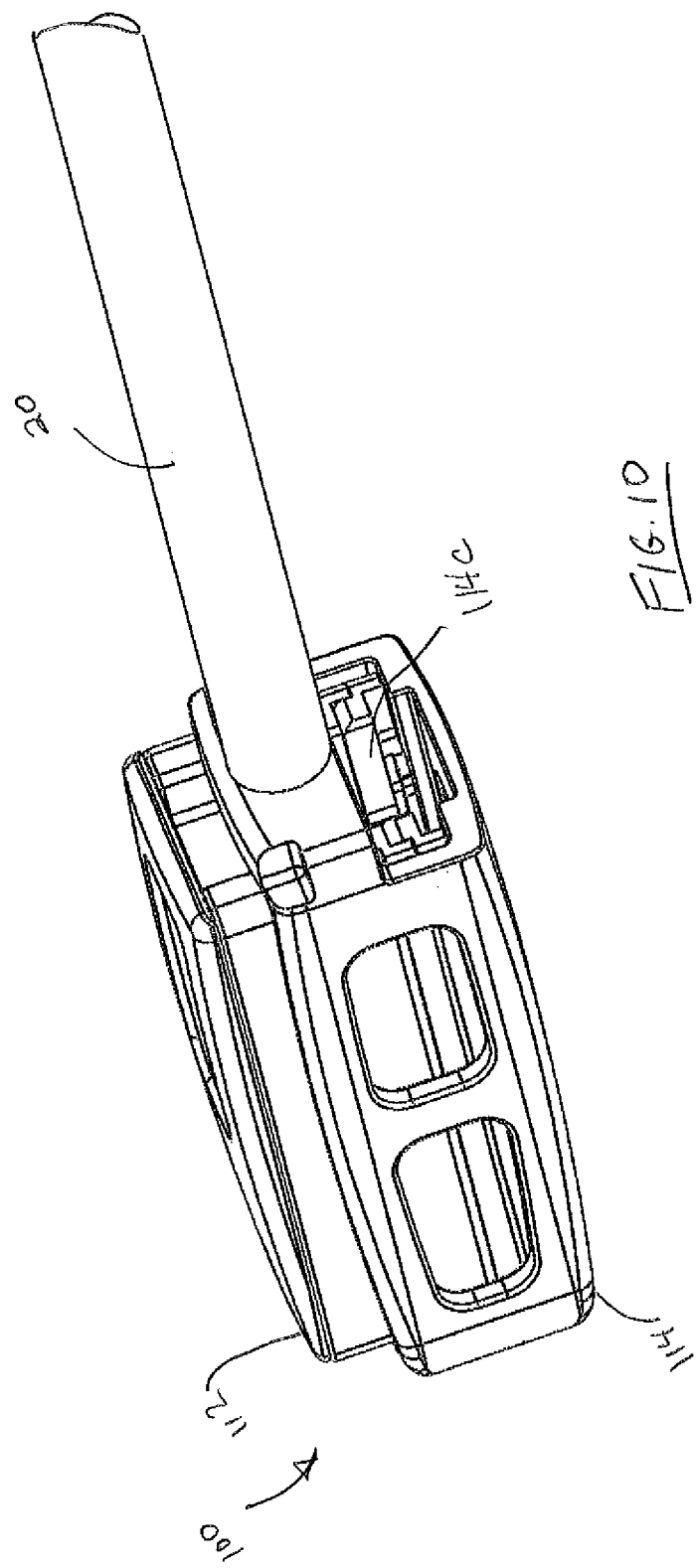
FIG. 10 is a proximal perspective view of an expanded spinal interbody fusion device with a guide pin releasably connected thereto subsequent to the inserter having been the detached from the guide pin with inserts not being shown for clarity.

It should be appreciated that when upon operation of trigger actuator 14 lifting platform 24 is incapable of physically reaching the desired elevation (which is approximately slightly greater than the thickness of an insert 200 and determined by the bar linkage mechanism 31), further operation of the trigger actuator 14 during any given stroke will be substantially prevented. Such resistance will provide tactile feedback to the surgeon who will recognize that the device 100 has been expanded to its maximum anatomic extent as the spine has reached ligamentotaxis. The surgeon would then terminate the insert insertion procedure releasing handle 36, and then removing the inserter 10 from the expanded device 100 by rotatably removing knob 22 from the proximal end of guide pin 20. As shown in FIG. 10, the guide pin 20 may remain releasably connected to expanded device 100 to serve as a locator for subsequent attachment to an apparatus containing suitable bone growth material to assist in the delivery of such material into a channel 114c of inferior endplate 114 through which inserts 200 were inserted.

Having described the inserter 10 and the method of expanding an interbody fusion device 100 and inserting thereinto one or more inserts 200 with reference to device 100 wherein a first insert 200 has been positioned between superior endplate 112 and inferior endplate 114, it should be appreciated that the inserter 10 and method may also be used to introduce insert 200 initially between superior endplate 112 and inferior endplate 114.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, while the lifting platform 24 has been described herein as being movable axially relative to a fixed elevator 26, it should be appreciated that lifting platform 24 may be held in a fixed axial position while the elevator 26 is moved axially relative thereto. Also, while the illustrated embodiments have been directed particularly to interbody fusion of the spine, the expandable devices and inserts disclosed herein may be used in other applications that require distraction of tissue surfaces, such as, for example, vertebral compression fracture treatments. Modifications in size may be necessary depending upon the body space being distracted.

What is claimed is:

1. An inserter for expanding an expandable spinal interbody fusion device and inserting an insert therewithin, said device including a superior endplate having an outer surface configured to contact a first vertebral body of a spine and an inferior endplate movable relative to said superior endplate in an expansion direction, said inferior endplate having an outer surface configured to contact a second opposing vertebral body of said spine, comprising:
   an elongate barrel having a distal end and a proximal end, said distal end being releasably attachable to said device and comprising a trigger actuator at said proximal end,
   said barrel including at said distal end a lifting platform for engaging said superior endplate and an elevator for engaging said inferior endplate, said lifting platform being movable translationally relative to said elevator in a direction transverse to the direction of expansion of said device to cause during such translational movement said lifting platform to move away from said elevator in the direction of expansion and thereby lift said lifting platform relative to said inferior endplate and expand said device, one of said lifting platform and said elevator being operably coupled to said trigger actuator to cause said translational movement upon operation of said trigger actuator, and
   said barrel movably supporting at least one insert insertable upon operation of said trigger actuator into said device between said superior endplate and said inferior endplate after expansion of said device, said barrel supporting a driver coupled to said trigger actuator for translational movement relative to one of said lifting platform and said elevator, said driver having a distal end defining a pushing surface for engagement with a cooperative pushing surface on said insert.

2. The inserter of claim 1, wherein said lifting platform and said elevator comprise cooperating ramps that upon relative translation of said lifting platform and said elevator cause said ramps to cooperatively engage and move said lifting platform and said elevator relatively away from each other in the direction of expansion.

3. The inserter of claim 2, wherein said lifting platform is coupled to said trigger actuator for translational movement and said elevator is attached to said barrel in a fixed position.

4. The inserter of claim 3, wherein said driver is coupled to said trigger actuator for translational movement relative to said elevator.

5. The inserter of claim 4, wherein said lifting platform includes an upper surface for supporting said insert and a lower opposing surface defining said cooperating ramps.

6. The inserter of claim 5, wherein said driver and said lifting platform are coupled to said trigger actuator to move independently upon operation of said trigger actuator.

7. The inserter of claim 6, wherein said driver and said lifting platform are coupled to said trigger actuator to move independently of each other upon operation of a single stroke of said trigger actuator.

8. The inserter of claim 7, wherein said lifting platform is coupled to said trigger actuator to move before movement of said driver and cause said superior endplate to lift relative to said inferior endplate.

9. The inserter of claim 8, wherein said lifting platform is coupled to said trigger actuator to hold the position of said superior endplate in a lifted position relative to said inferior endplate during operation of said trigger actuator while said driver is moved during such operation to push said insert at least partially between said superior endplate and said inferior endplate.

10. The inserter of claim 9, wherein said lifting platform is coupled to said trigger actuator to retract said lifting platform towards said elevator after said insert is positioned at least partially between said superior endplate and said inferior endplate, said driver being coupled to said trigger actuator to advance said insert thereafter substantially fully between said superior endplate and said inferior endplate.

11. The inserter of claim 10, wherein said lifting movement of said lifting platform relative to said elevator, said translational movement of said driver insert for pushing said insert into said device and said retraction movement of said lifting platform towards said elevator are effected in a single operational stroke of said trigger actuator.

12. The inserter of claim 11, wherein said trigger actuator comprises a linkage mechanism that substantially prevents translational movement of said driver until the lifting movement of said lifting platform is completed.

13. The inserter of claim 12, wherein said barrel movably supports a further insert insertable upon operation of said trigger actuator between said at least first insert and said inferior endplate.

14. An apparatus for use in spinal interbody fusion, comprising:
   an expandable interbody fusion device including an inferior endplate having an outer surface configured to contact a vertebral body of the spine, a superior endplate having an outer surface configured to contact an opposing vertebral body of said spine, said inferior endplate and said superior endplate being movable relative to each other in a direction of expansion, said device including at least one insert insertable into said device between said inferior endplate and said superior endplate upon expansion of said device; and
   an elongate inserter having a distal end and a proximal end, said distal end of said inserter being releasably attached to said device, said inserter including an actuator at said proximal end, said inserter comprising a lifting platform disposed between said inferior endplate and said superior endplate and operably coupled to said actuator for lifting one of said superior endplate and an insert within said device, and a driver operably coupled to said actuator to insert said at least one insert into said device, said inserter including an elongate track linearly supporting a plurality of inserts for sequential insertion into said device one below the other.

15. The apparatus of claim 14, wherein said inserter comprises an elevator at said distal end, said elevator having an upper surface and a lower surface, said lower surface being in engagement with an interior surface of said inferior endplate.

16. The apparatus of claim 15, wherein said lifting platform has a lower surface, the lower surface of said lifting platform and the upper surface of said elevator comprising cooperatively engaging ramps.

17. The apparatus of claim 16, wherein said elevator is disposed in a fixed position relative to said inferior endplate and said lifting platform is coupled to said actuator for translational movement relative to said elevator upon operation of said actuator to cause said ramps to cooperatively engage and thereby move said lifting platform and said elevator relatively away from each other in the direction of expansion.

18. The apparatus of claim 14, wherein said actuator comprises a trigger actuator including a handle and a bar linkage mechanism pivotally coupled thereto.

19. The apparatus of claim 14, wherein said apparatus further comprises a guide pin releasably connected to said device and detachably connected to said inserter.

20. The apparatus of claim 14, wherein said at least one insert comprises a locking structure to interlock said at least one insert to said superior endplate upon insertion into said device.

21. The apparatus of claim 20, wherein said at least one insert comprises a locking structure to interlock said at least one insert to a subsequent insert inserted below said at least one insert.

22. A method of expanding an expandable spinal interbody fusion implant, in situ, said device including an inferior endplate having an outer surface configured to contact a vertebral body of the spine, a superior endplate having an outer surface configured to contact an opposing vertebral body of said spine, said inferior endplate and said superior endplate being movable relative to each other in a direction of expansion, comprising the steps of:
  releasably attaching a distal end of an inserter to said device, said inserter including an actuator at a proximal end thereof;
  initially operating said actuator to cause said inferior endplate and said superior endplate to move relative to each other in a direction of expansion to expand said device; and
  inserting a first insert movably supported by said inserter into said device after expansion of said device between said inferior endplate and said superior endplate; and then
  further operating said actuator to cause said superior endplate and said first insert to move jointly relative to said inferior endplate to further expand said device, and after said further expansion sequentially inserting a second insert movably supported by said inserter directly between said first insert and said inferior endplate.

23. The method of claim 22, wherein said first insert and said second insert are supported linearly by said inserter immediately adjacent each other, and wherein after said device is expanded in the initial operating step said first insert is inserted directly between said superior endplate and said inferior endplate.

24. The method of claim 23, further including the step of determining whether said expanded device is capable of receiving a further insert prior to insertion of said further insert between said inferior endplate and said superior endplate.

25. The method of claim 24, wherein said determining step is effected by tactile feedback through said actuator.

26. The method of claim 25, wherein said actuator comprises a trigger actuator including a handle and a linkage mechanism, and wherein the expansion of said device and the insertion of said at least one insert into said expanded device is effected in a single operational stroke of said trigger actuator.

27. A method of expanding an expandable spinal interbody fusion implant, in situ, said device including an inferior endplate having an outer surface configured to contact a vertebral body of the spine, a superior endplate having an outer surface configured to contact an opposing vertebral body of said spine, said inferior endplate and said superior endplate being movable relative to each other in a direction of expansion, comprising the steps of:
  releasably attaching a distal end of an inserter to said device, said inserter including an actuator at a proximal end thereof and an elongate track therebetween supporting a plurality of inserts, each insert having a thickness in the direction of expansion;
  operating said actuator for the individual insertion of said plurality of inserts, during said operation causing the inferior endplate and the superior endplate to move apart relative to each other in the direction of expansion independently of the insertion of each insert and creating for each insert an incremental space in the expanded device of dimension not less than the thickness of an insert; and
  sequentially individually inserting said plurality of inserts into a respectively created incremental space.

28. The method of claim 27, wherein a first incremental space is created directly between said inferior endplate and said superior endplate for the insertion of a first insert.

29. The method of claim 28, wherein a second incremental space is created directly between said inferior endplate and said first insert for the insertion of a second insert, said first insert and said superior endplate having been moved jointly relative to said inferior endplate upon the operation of said actuator.

30. The method of claim 29, further including the step of determining whether said expanded device is capable of receiving a third insert prior to insertion of said third insert between said inferior endplate and said second insert as determined by tactile feedback through said actuator.

* * * * *